(12) United States Patent
Ravikumar et al.

(10) Patent No.: US 11,515,013 B2
(45) Date of Patent: Nov. 29, 2022

(54) METHOD AND SYSTEM FOR IN-SILICO OPTIMIZATION AND DESIGN OF ELECTROLYTES

(71) Applicant: Tata Consultancy Services Limited, Mumbai (IN)

(72) Inventors: Bharath Ravikumar, Pune (IN); Beena Rai, Pune (IN); Mahesh Mynam, Pune (IN); Sravani Repaka, Pune (IN); Surbhikumari Ashutosh Kumar, Pune (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 320 days.

(21) Appl. No.: 16/834,895

(22) Filed: Mar. 30, 2020

(65) Prior Publication Data

US 2020/0321080 A1 Oct. 8, 2020

(30) Foreign Application Priority Data

Apr. 5, 2019 (IN) .............................. 201921013835

(51) Int. Cl.
| | |
|---|---|
| *G16C 20/60* | (2019.01) |
| *G16C 20/50* | (2019.01) |
| *G06F 30/20* | (2020.01) |
| *H01M 10/056* | (2010.01) |

(52) U.S. Cl.
CPC ............. *G16C 20/60* (2019.02); *G06F 30/20* (2020.01); *G16C 20/50* (2019.02); *H01M 10/056* (2013.01)

(58) Field of Classification Search
CPC .............................. G06F 30/20; H01M 10/056
See application file for complete search history.

(56) References Cited

U.S. PATENT DOCUMENTS

| | | | |
|---|---|---|---|
| 8,301,285 B2 | 10/2012 | Zhang et al. | |
| 2009/0326696 A1* | 12/2009 | Wang ................. | H01M 10/052 700/106 |

FOREIGN PATENT DOCUMENTS

| | | |
|---|---|---|
| JP | 2011-232805 | 11/2011 |
| KR | 10-0918387 | 9/2009 |

* cited by examiner

*Primary Examiner* — Michael Jung
(74) *Attorney, Agent, or Firm* — Finnegan, Henderson Farabow, Garrett & Dunner, LLP

(57) ABSTRACT

Owing to complexity of the algorithms and tools very few attempts have been seen for usage of simulation methods in the development of new electrolytes. Moreover, the existing simulation methods focus on only one aspect of the electrolyte at a time and this limits accuracy of simulation results, and affects performance of electrolyte in real world, where multiple factors come into play simultaneously. The method disclosed provides method and system for in-silico optimization and design of electrolytes, enabling prediction of various properties of an electrolytic mixture of salts, solvents and various additives and its suitability for a given battery technology. The in-silico method shapes itself into an overall battery electrolyte property or component composition analyzer based on the user input.

15 Claims, 11 Drawing Sheets

METHOD AND SYSTEM FOR IN-SILICO OPTIMIZATION AND DESIGN OF ELECTROLYTES

PRIORITY CLAIM

This U.S. patent application claims priority under 35 U.S.C. § 119 to: Indian provisional patent application no. 201921013835, filed on Apr. 5, 2019. The entire contents of the aforementioned application are incorporated herein by reference.

TECHNICAL FIELD

The disclosure herein generally relates to electrolyte design, and, more particularly to, method and system for in-silico optimization and design of electrolytes.

BACKGROUND

The emergence of electric vehicles and grid storage systems demand for faster development cycles of advanced batteries offering superior properties such as quicker charging rate, large capacity, long life and extreme safety. Electrolytes used in the batteries play a critical part in safety, cycle life and battery performance. Research and development is being focused on designing efficient and high performance electrolytes. Lithium—ion battery is one such example of batteries used for above applications such as electric vehicles. Thus, designing the electrolyte that provides the best performance for a particular battery type (e.g., based on lithium, sodium, nickel, cadmium, magnesium and so on) is required to achieve desired battery performance.

Electrolytes used in the batteries are typically mixtures of salts and solvents, along with a set of performance enhancing additives. Electrolytes provide a passive contact between the two electrodes in a cell to facilitate the movement of ions from one electrode to the other during the charge-discharge cycles. In addition to playing the role in circuit completion, electrolytes also determine the operating conditions of a battery, including safe voltage window, temperature range, charging protocol, etc. Battery electrolyte needs to be designed to offer optimum values for several key properties. The electrolyte needs to be cost-effective, non-toxic and should not lead to unwanted side-reactions. Hence, the design and development of electrolytes for various advanced battery technologies is more challenging than before. It deals with various expensive and time-consuming spectroscopic, microscopic imaging techniques and electrochemical methods.

Conventional methods used for electrolyte design include selection of components and optimization. These methods heavily rely on experimentation involving trial and error procedure and are sequential and time-consuming. Since, the progress of in-situ analysis is slow, the verification of different properties involves various sophisticated instruments that require various ways of sample preparation. Hence, the conventional methods are not flexible. Further, existing approach for electrolyte screening is based on a very narrow set of objectives. Most of the existing studies to evaluate the capability of an electrolyte are conductivity-centric that talk about its charge transferring capabilities alone.

Advent of high-performance computing (HPC) systems and various simulation algorithms enable one to conduct virtual experiments to evaluate various properties by simulating the system of interest at various length and time scales. However, owing to the involved complexity of the algorithms and tools and required analysis, use of simulation methods in the development of new electrolytes is limited. Identification of the right components to be used in the electrolyte mixture for a given battery itself is a complex task. Determining the optimal proportion of the identified components makes the task even more complicated. Experimental approach to address this problem is very expensive and time consuming.

SUMMARY

Embodiments of the present disclosure present technological improvements as solutions to one or more of the above-mentioned technical problems recognized by the inventors in conventional systems. For example, in one embodiment, a method for in-silico optimization and design of electrolytes is provided. The method comprises displaying a User Interface (UI), implemented by one or more processors, to receive at least one user input, wherein the UI provides: a user requirement module for specifying a first user input comprising 1) a battery from a list of battery types and 2) a user requirement from a list of requirements indicating a user objective related to an electrolyte to be designed for use in the battery, wherein performance of the battery is to be optimized for the user requirement specified for the electrolyte; a component selection module for specifying a second user input comprising components of the electrolyte to be used for the battery, wherein the components comprise 1) one or more salts, 2) one or more solvents, and 3) additives; an operating parameters module to select a third user input comprising one or more operating parameters; and a constraints module for specifying a fourth user input comprising constraints on values of one or more properties of the electrolyte.

Further, the method comprises selecting, via an initiation module implemented by the one or more processors, a simulation module from a plurality of simulation modules providing molecular modeling simulations, wherein selection of the simulation module is based on the user requirement specified in the user requirement module.

Further, the method comprises performing, using the selected simulation module implemented by the one or more processors, simulation to create simulation files, in accordance with the battery, the salts, the one or more solvents and the additives.

Furthermore, the method comprises executing, using a solver module implemented by the one or more hardware processors, the simulation files in accordance with the user requirement, the one or more operating parameters and the constraints on values of the one or more properties of the electrolyte, wherein the execution of simulation files provides a plurality of simulation output data files capturing variation of one or more properties of the electrolyte against the user requirement, and wherein the simulation files are re-executed, by an optimization module implemented by the one or more hardware processors, until the one or more properties of the electrolyte are satisfied when the user requirement specifies requirement of optimal battery performance against the specified at least one user inputs.

Furthermore, the method comprises displaying on the UI a set of simulation output data files from the plurality of simulation output data files that provide the optimal battery performance, wherein the simulation output datafiles are stored for future reference.

In another aspect, a system for in-silico optimization and design of electrolytes is provided. The system comprises a memory storing instructions; one or more Input/Output (I/O) interfaces; and one or more hardware processor(s) coupled to the memory via the one or more I/O interfaces, wherein the processor(s) is configured by the instructions to display a User Interface (UI), implemented by the one or more processors, to receive at least one user input, wherein the UI provides: a user requirement module for specifying a first user input comprising 1) a battery from a list of battery types and 2) a user requirement from a list of requirements indicating a user objective related to an electrolyte to be designed for use in the battery, wherein performance of the battery electrolyte is to be optimized for the user requirement specified for the electrolyte; a component selection module for specifying a second user input comprising components of the electrolyte to be used for the battery, wherein the components comprise 1) one or more salts, 2) one or more solvents, and 3) additives; an operating parameters module to select a third user input comprising one or more operating parameters; and a constraints module for specifying a fourth user input comprising constraints on values of one or more properties of the electrolyte.

Further, the one or more hardware processors are configured to selecting, via an initiation module implemented by the one or more processors, a simulation module from a plurality of simulation modules providing molecular modeling simulations, wherein selection of the simulation module is based on the user requirement specified in the user requirement module.

Further, the one or more hardware processors are configured to perform, using the selected simulation module implemented by the one or more processors (104), simulation to create simulation files, in accordance with the battery, the salts, the one or more solvents and the additives.

Furthermore, the one or more hardware processors are configured to execute, using a solver module implemented by the one or more hardware processors, the simulation files in accordance with the user requirement, the one or more operating parameters and the constraints on values of the one or more properties of the electrolyte, wherein the execution of simulation files provides a plurality of simulation output data files capturing variation of one or more properties of the electrolyte against the user requirement, and wherein the simulation files are re-executed, by an optimization module implemented by the one or more hardware processors, until the one or more properties of the electrolyte are satisfied when the user requirement specifies requirement of optimal battery performance against the specified at least one user inputs.

Furthermore, the one or more hardware processors are configured to display on the UI a set of simulation output data files from the plurality of simulation output data files that provide the optimal battery performance, wherein the simulation output datafiles are stored for future reference.

In yet another aspect, they are provided one or more non-transitory machine-readable information storage mediums comprising one or more instructions, which when executed by one or more hardware processors causes a method for in-silico optimization and design of electrolytes. Further, the method comprises displaying a User Interface (UI), implemented by one or more processors, to receive at least one user input, wherein the UI provides: a user requirement module for specifying a first user input comprising 1) a battery from a list of battery types and 2) a user requirement from a list of requirements indicating a user objective related to an electrolyte to be designed for use in the battery, wherein performance of the battery is to be optimized for the user requirement specified for the electrolyte; a component selection module for specifying a second user input comprising components of the electrolyte to be used for the battery, wherein the components comprise 1) one or more salts, 2) one or more solvents, and 3) additives; an operating parameters module to select a third user input comprising one or more operating parameters; and a constraints module for specifying a fourth user input comprising constraints on values of one or more properties of the electrolyte.

Further, the method comprises selecting, via an initiation module implemented by the one or more processors, a simulation module from a plurality of simulation modules providing molecular modeling simulations, wherein selection of the simulation module is based on the user requirement specified in the user requirement module.

Further, the method comprises performing, using the selected simulation module implemented by the one or more processors (104), simulation to create simulation files, in accordance with the battery, the one or more salts, the one or more solvents and the additives.

Furthermore, the method comprises executing, using a solver module implemented by the one or more hardware processors, the simulation files in accordance with the user requirement, the one or more operating parameters and the constraints on values of the one or more properties of the electrolyte, wherein the execution of simulation files provides a plurality of simulation output data files capturing variation of one or more properties of the electrolyte against the user requirement, and wherein the simulation files are re-executed, by an optimization module implemented by the one or more hardware processors, until the one or more properties of the electrolyte are satisfied when the user requirement specifies requirement of optimal battery performance against the specified at least one user inputs.

Furthermore, the method comprises displaying on the UI a set of simulation output data files among the plurality of simulation output data files that provide the optimal battery performance, wherein the simulation output datafiles are stored for future reference.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION OF EMBODIMENTS

Figure 1:
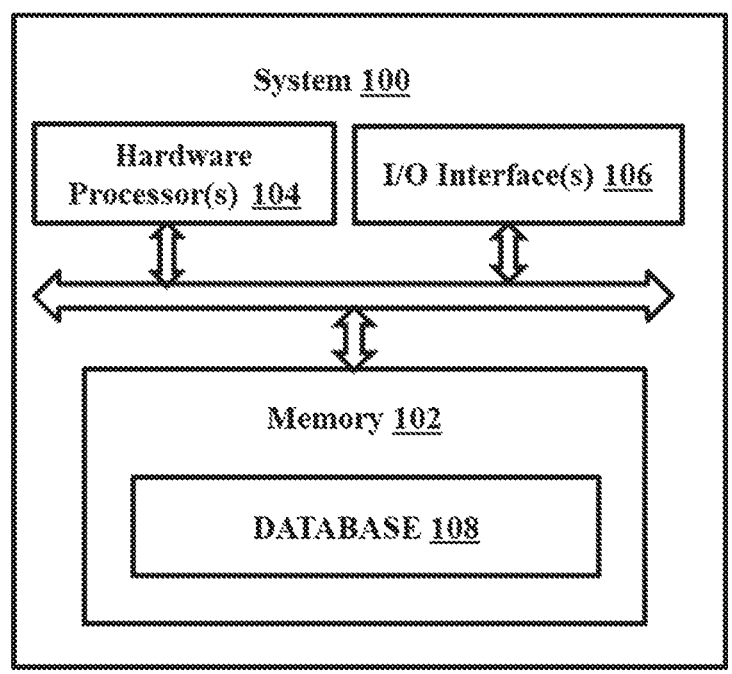
FIG. 1 is a functional block diagram of a system for in-silico optimization and design of electrolytes, in accordance with some embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following claims.

Apart from cost of money and time, the prior systems find it difficult tackle the intricacies testing electrolytes in operating environments which are difficult to be created in a laboratory scale.

The embodiments herein provide a method and system for in-silico optimization and design of electrolytes. The method and system disclosed provides a framework for prediction of various properties of an electrolytic mixture of salts, solvents and various additives and its suitability for a given battery technology. The framework shapes itself into an overall battery electrolyte property or composition analyzer based on the user input requirements. The method comprises of several modules interconnected based on workflows to provide the ideal set electrolytes for the operational requirement for any battery. Further, the methods comprise sub-methods or tools that provide advice on favorable or optimal operating conditions for obtaining the best performance out of an electrolyte.

Referring now to the drawings, and more particularly to FIGS. 1 through 6, where similar reference characters denote corresponding features consistently throughout the figures, there are shown preferred embodiments and these embodiments are described in the context of the following exemplary system and/or method.

FIG. 1 is a functional block diagram of a system 100 for in-silico optimization and design of electrolytes, in accordance with some embodiments of the present disclosure.

In an embodiment, the system 100 includes a processor(s) 104, communication interface device(s), alternatively referred as or input/output (I/O) interface(s) 106, and one or more data storage devices or memory 102 operatively coupled to the processor(s) 104. The processors(s) 104, can be one or more hardware processors 104. In an embodiment, the one or more hardware processors can be implemented as one or more microprocessors, microcomputers, microcontrollers, digital signal processors, central processing units, state machines, logic circuitries, and/or any devices that manipulate signals based on operational instructions. Among other capabilities, the processor(s) is configured to fetch and execute computer-readable instructions stored in the memory. In an embodiment, the system 100 can be implemented in a variety of computing systems, such as laptop computers, notebooks, hand-held devices, workstations, mainframe computers, servers, a network cloud and the like.

The I/O interface(s) 106 can include a variety of software and hardware interfaces, for example, a web interface, a user interface (UI), and the like and can facilitate multiple communications within a wide variety of networks N/W and protocol types, including wired networks, for example, LAN, cable, etc., and wireless networks, such as WLAN, cellular, or satellite. In an embodiment, the I/O interface device(s) can include one or more ports for connecting a number of devices to one another or to another server. The UI is configured to display a plurality of modules to enable user to provide one or more initial user inputs to the system 100. The modules are stored in the memory 102 and explained in conjunction with method steps of FIG. 2.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. The memory 102, may further store a data set that may be received from external sources via the I/O interface(s) 106, such as the user inputs through the UI. Further, the memory 102 may include a database 108, which can store a plurality of simulation modules, a plurality of mapping tables, behavior and specifications for a plurality of battery types defining battery models and the like in the database 108. Further, the memory 102 may comprise information pertaining to input(s)/output(s) of each step performed by the one or more hardware processor (s) 104 of the system 100 and methods of the present disclosure.

The system 100 provides the following features for efficient analysis and accurate inference of the electrolyte properties:

1) An in-silico method providing end-to-end application framework for design and optimization of electrolyte. The system 100 receives user inputs, wherein required details can be either filled by the user independently or selected from choices provided in the tool. Once the required data is submitted, the system 100 automates the entire process of design and optimization of the electrolyte, until, results are obtained. The user has the choice of accepting the results or rerun the whole session (method steps) until the results are satisfactory.

2) Identification of the right combination—Knowing the effects of change in the composition of the electrolyte on various properties of the electrolyte are crucial for design of electrolytes for high performance batteries. The framework enables the identification of the right combination of materials for a given battery electrolyte and its operating environment. The framework also provides an option to account for the effect of ageing of battery, which typically leads to degradation of various components of electrolytes, while designing or optimizing the composition of the electrolyte for a given battery. Effect of aging on electrolyte composition can be an input or otherwise, system implements typical degradation mechanisms applicable for the given class of electrolytes.

3) Cognizance of the operating conditions—The electrolyte properties are evaluated for the operating conditions of the specific battery and chosen test conditions the user is interested in, for example, the temperature, pressure, etc.

4) Advice on the suitable working conditions—Based on the evaluation of the properties, the framework identifies and suggests the suitable operating regime for the specified battery system. For example, the temperature window the electrolyte can be operated at, the concentration of an additive or some other compound it can tolerate and so on.

5) Ranking of additives—It provides a way to rank various additives based on their impact on one or more properties of importance to qualify them as the performance enhancers in the context of viscosity reduction, thermal stability, power performance improvements and so on. For example, a list of additives can be given ordered on the basis of the improvement in the ionic conductivity it can provide for the electrolyte system.

The features of the system disclosed, are explained in conjunction with multiple use case scenarios stating different user requirements for a battery type, typically secondary lithium ion batteries as an example and may not be construed as a limitation. However, any battery type can be selected in accordance with the data for a multitude of battery types stored in the database 108 of the system and may not be construed as limitation. The features are explained through examples in conjunction with method of FIG. 2A and FIG. 2B.

Further, it can be understood by ordinary person skilled in the art that even though the description describes the electrolyte design and optimization for battery electrolyte, it can be applied for electrolyte design and optimization for other electrolyte based systems, wherein the behavior and specifications of the other electrolyte based systems can be modeled and stored in the database 108, to be used during the simulation process.

Figure 2A:
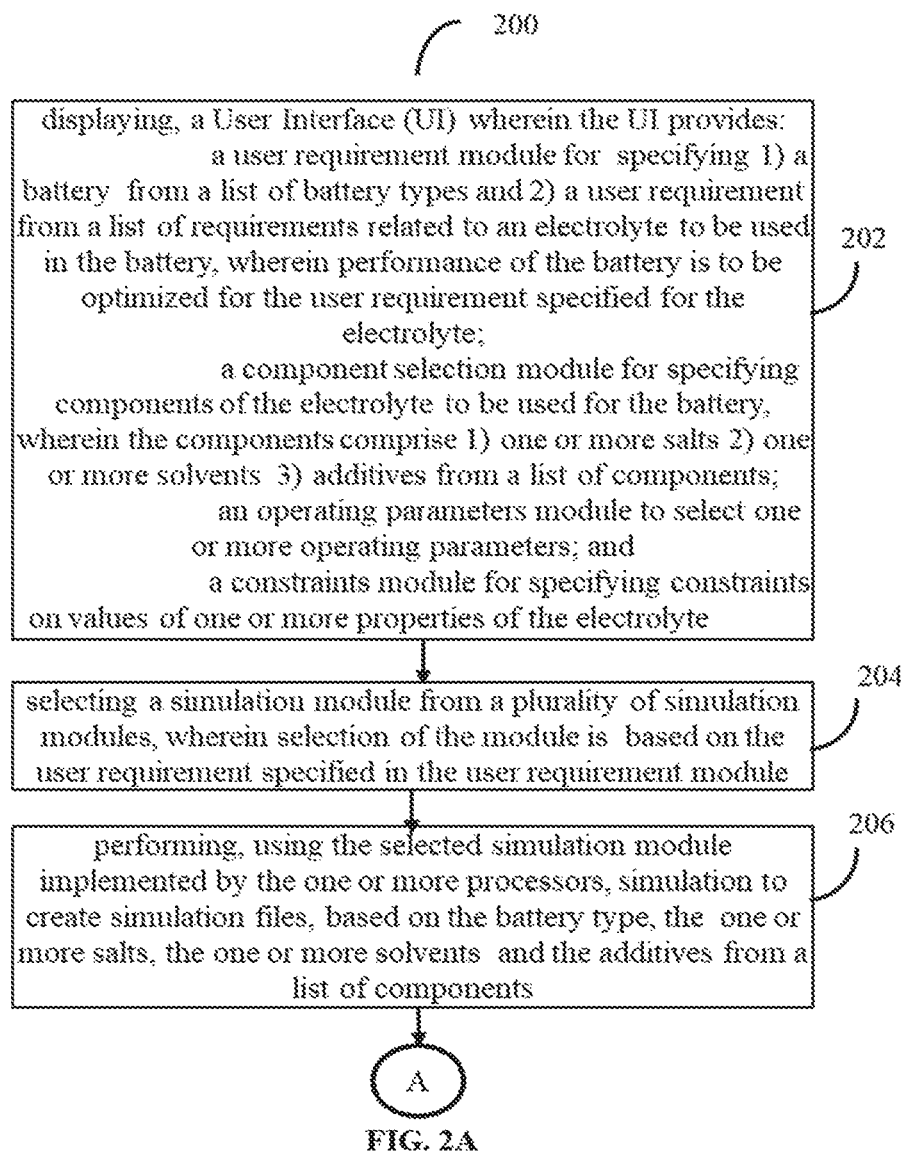
FIG. 2A and FIG. 2B is a flow diagram illustrating a method for in-silico optimization and design of electrolytes using system of FIG. 1, in accordance with some embodiments of the present disclosure.
Figure 2B:
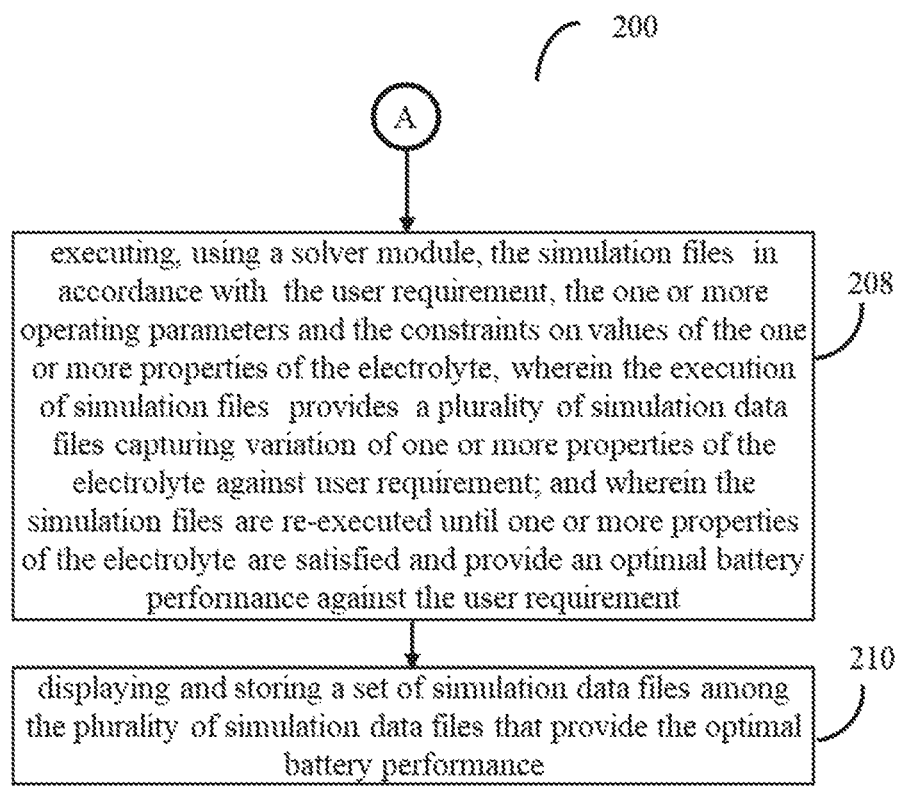

FIG. 2A and FIG. 2B is a flow diagram illustrating a method 200 for in-silico optimization and design of electrolytes implemented by the system 100 of FIG. 1, in accordance with some embodiments of the present disclosure.

In an embodiment, the system 100 comprises one or more data storage devices or the memory 102 operatively coupled to the processor(s) 104 and is configured to store instructions for execution of steps of the method 200 by the processor (s) 104. The steps of the method 200 of the present disclosure will now be explained with reference to the components or blocks or modules of the system 100 as depicted in FIG. 1 and the steps of flow diagram as depicted in FIG. 2A and FIG. 2B. Although process steps, method steps, techniques or the like may be described in a sequential order, such processes, methods and techniques may be configured to work in alternate orders. In other words, any sequence or order of steps that may be described does not necessarily indicate a requirement that the steps to be performed in that order. The steps of processes described herein may be performed in any order practical. Further, some steps may be performed simultaneously.

Referring to the steps of the method 200, in an embodiment of the present disclosure, at step 202, the one or more hardware processor(s) 104 are configured to display the UI implemented by one or more hardware processors 104, to receive at least one user input. The UI provides:

a) a user requirement module for specifying a first user input comprising 1) a battery from a list of battery types and 2) a user requirement from a list of requirements indicating a user objective related to an electrolyte to be designed for use in the battery, wherein performance of the battery is to be optimized for the user requirement specified for the electrolyte;

b) a component selection module for specifying a second user input comprising components of the electrolyte to be used for the battery, wherein the components comprise 1) one or more salts, 2) one or more solvents, and 3) additives from a list of components or can be newly added by the user;

c) an operating parameters module to select a third user input comprising one or more operating parameters; and d) a constraints module for specifying a fourth user input comprising constraints on values of one or more properties of the electrolyte. The one or more properties of the electrolyte comprise bulk physical properties and dynamic properties of the electrolyte.

The UI design of each module is done using known UI design technology to provide drop down menus, editable entry tabs, selection/radio buttons and so on.

At step 204 of the method 200, the one or more hardware processor(s) 104 are configured to select via an initiation module implemented by the one or more processors 104, a simulation module from a plurality of simulation modules, wherein selection of the module is based on the input requirement specified in the user requirement module. A plurality of simulation modules providing molecular modeling simulations and utilizes Density Functional Theory (DFT), Molecular Dynamics (MD), Ab-initio Molecular Dynamics (AIMD), Meta-Dynamics, Monte Carlo (MC) simulations and so on present in the database 108 are mapped using mapping tables on specific user requirements. This feature is explained in conjunction with the use case examples provided below.

At step 206 of the method 200, the one or more hardware processor(s) 104 are configured to perform simulation, using the selected simulation modules implemented by the one or more processors 104, to create simulation data files, in accordance with the battery type and the electrolyte components.

At step 206 of the method 200, the one or more hardware processor(s) 104 are configured to executing (208), using a solver module implemented by the one or more hardware processors, the simulation files in accordance with the input requirement, the one or more operating parameters and the constraints on values of the one or more properties of the electrolyte.

The execution of simulation files provides a plurality of simulation output data files capturing variation of one or more properties of the electrolyte against input requirement. Further, the simulation files are re-executed by an optimization module implemented by the one or more hardware processors 104 until one or more properties of the electrolyte are satisfied when the user requirement specifies an optimal battery performance against the specified at least one user inputs. The plurality of simulation output data files is generated in accordance with a set of predefined processes followed during the execution of the simulation files. The predefined processes specify the logic to compute values of each of the plurality of properties associated with the electrolyte. Thus, during execution of the steps of method 200 for the user requirement specifying the user objective, relevant or necessary one or more properties are analyzed using predefined processes corresponding to the property. The predefined processes may be stored as process modules in database 108. Few examples of properties and the technical steps used by the predefined modules to compute the values of these properties in conjunction with the type of simulation module used are described later.

At step 206 of the method 200, the one or more hardware processor(s) 104 are configured to display on the UI a set simulation output data files among the plurality of simulation output data files that provide the optimal battery performance.

A representative session of the method 200 implemented by the framework provided by the system 100 is described. The execution starts with the user entering the user inputs in user requirements module. This user requirements module identifies the objective of the simulation based on the user inputs (specifically the user requirements provided by the user. The user can state his objective as optimization of the electrolyte components for a required application, evaluation of properties for a set of electrolyte components or assessment of suitable operating conditions. The user can enter the existing data with respect to the electrolyte, the type of battery, etc. Further, the component selection module, enables selecting a range of components from the list of salts, solvents and additives. If components of interest are not available, the user can create the components by providing the chemical structure details in a suitable form required by the simulation modules to run, which can be prompted by the framework (system 100). Once the components of the electrolytes to be tested are provided, the session moves to the operating parameters module, where the operating conditions (e.g., Temperature, Pressure) in which the behavior of electrolyte has to be tested can be provided. After this, the session progresses to the constraints, where user can provide the constraints with respect to the properties (e.g. the minimum viscosity, maximum ionic conductivity) of the final mixture of the electrolyte for optimizing the composition. The user can also mention the properties that should not be altered while the evaluation is done. The composition of the electrolyte can be provided here for the initial simulation. This indicates, the composition, for which properties have to be analyzed when the objective is 'property analysis'. The set of properties to be evaluated can be provided here. The simulation specific parameters can also be entered here. The session further progresses to the solver module, where all the pre-processing of data for the simulations, the simulations themselves and post-processing is performed. The initiation module selects the most appropriate simulation module to be used to simulate the selected electrolyte for a typical input requirement that can be obtained from a mapping table, wherein different simulations modules are mapped against different user requirements. The sequence of simulation modules can be determined and defined by an expert based on the efficiency and accuracy, of different simulation modules/ techniques such as DFT, MD, MC etc., in finding properties that are relevant to provide results for the user requirement. Based on the user requirement, the system 100, can involve the sequence of one or more appropriate simulation modules, which are stored in the database 108.

Further, the solver module provides the list of properties evaluated at the end of the session. If satisfied, the user can exit the session.

However, when the objective is optimization, the obtained properties are verified against the constraints by triggering the optimization module. If they are not satisfied, the session can return to the constraints and initialization module, where the user can tweak the existing values if required. If not needed, the user can skip this step and the session continuously performs back and forth between the optimization and solver modules. The simulations are done for several combinations of the salt concentration, solvent ratios and additive composition etc. based on requirement. Once the constraints are satisfied, the session writes all the output data to the memory and exits.

The present disclosure treats the electrolyte of interest within the molecular modeling framework to compute or predict properties of importance. They include viscosity, density, dielectric constant, diffusivity, conductivity, degree of dissociation, transference number, effective charge, and mobility under external electric fields, nature of the structures in the solution, types and charges of molecular clusters, dynamic behavior of clusters, residence or life time of clusters, migration time scales of active ion between various clusters, aging effects on the electrolyte conductivity and several other properties that are of interest to electrolyte designers or researchers. It repeats the exercise for a range of conditions to identify optimum conditions/composition that achieves the required properties. Also, it pre-processes the elements of individual compounds and provides appropriate parameters of the force field/potential functions, pseudopotentials or other essential models required for execution of molecular modeling simulations such as DFT, MD, AIMD, meta-dynamics, Monte Carlo and various other methods to simulate the electrolyte mixtures in an appropriate manner. Further, the present disclosure can help in screening/predicting additives or co-solvents and various other components of the electrolyte to reduce the number of experiments and cost associated with it.

Few examples of electrolyte design performed by the system 100 for varied user input requirements are stated below:

EXAMPLE 1

User Requirement (User Objective): Find the ionic conductivity of an electrolyte mixture composed of lithium hexafluorophosphate (LiPF6) salt in a solvent of ethylene carbonate (EC) at a salt concentration of 1 molar (1 M) for a lithium ion battery.

Modules Used: User Requirement Module, Component Selection Module, Operating Parameters Module, Constraints module and Initiation Module, Solver Module.

Procedure
1. User Requirement Module: Enter the requirement as "Property Analysis". Select the property 'Ionic Conductivity' from the list of properties. Enter the type of battery.
2. Component Module: Select the components of the electrolyte from the different database—
    a) LiPF6 from the list of salts.
    b) EC from the list of solvents.
Since the components are already present in the database user can select them. Otherwise, the user has to create an entry by providing all the required information.
3. Operating Parameters Module: Select the operating conditions—
    a) Temperature—320 K
    b) Pressure—1 atm
4. Initiation Module: Enter the salt concentration of the electrolyte mixture.
    Concentration—1 M Since the property to be evaluated is ionic conductivity, our framework chooses to do Molecular Dynamic (MD) simulations. The components were selected from the already existing database. Therefore, the input data file required for MD is created using a third-party tool. The data file includes the simulation box set up consisting of LiPF6 and EC molecules such that the salt concentration is 1 M.

5. Solver Module: MD simulation package such as LAMMPS, GROMACS, and TINKER etc. is selected to run these simulations. The simulation software provides trajectory files as output. These trajectory files are post-processed using the codes built in the system to evaluate the ionic conductivity.

Result: The ionic conductivity value of the electrolyte is displayed on the screen or written into the memory.

EXAMPLE 2

User Requirement (User Objective): To find out the maximum operating temperature of a 1 M $LiPF_6$ in a 3:7 solvent mixture of propylene carbonate (PC) and dimethyl carbonate (DMC) for lithium ion battery.

Modules Used: User Requirement Module, Component Selection Module, Operating Parameters Module, Constraints Module, Initiation Module, Solver Module.

Procedure

1. User Requirements Module: Enter the requirement as "Optimal Operating Condition". Select Temperature from the list. Enter the type of battery.
2. Component Selection Module: Select the components of the electrolyte from the database—
   a) $LiPF_6$ from the list of salts.
   b) PC and DMC from the list of solvents.
3. Operating Parameters Module: Pressure—1 atm.
4. Constraints Module: Select the limits of various properties that will affect the performance of the lithium ion battery such as
   1) Minimum Ionic Conductivity.
   2) Minimum and Maximum Viscosity
   3) Minimum Dielectric Constant of the solvent mixture
5. Initiation Module: The framework chooses to do MD simulations. The input files for MD having 3:7 PC/DMC bare solvent mixture and with a $LiPF_6$ salt concentration of 1 M are created.
6. Solver Module: The MD simulations analyze the various molecular interactions in terms of radial distribution function, coordination number, aggregate formation etc. The simulations calculate the properties listed in the Constraints module at various temperatures.

Result: The suitable operating range of the electrolyte is displayed on the screen or written into the memory.

EXAMPLE 3

Figure 3:
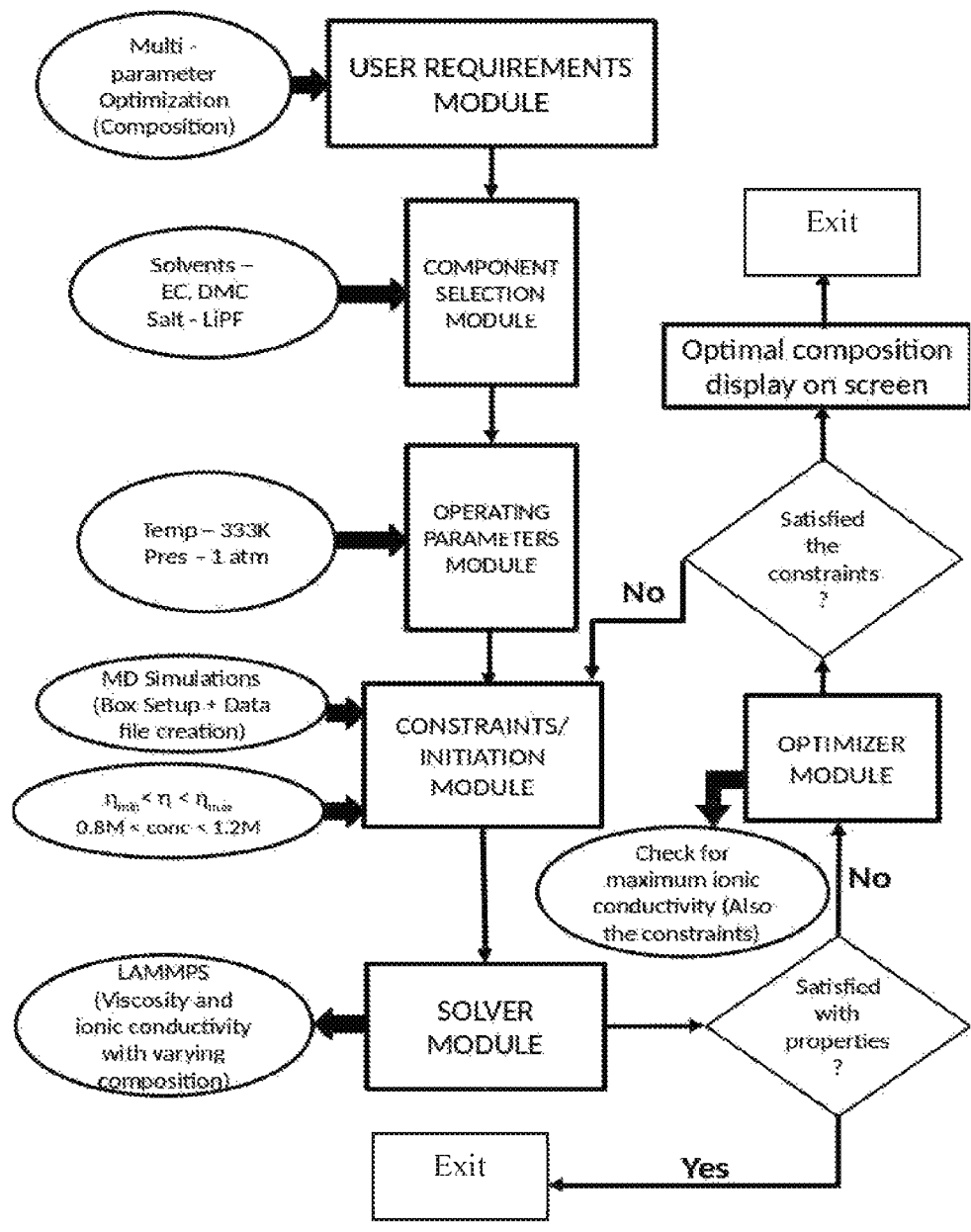
FIG. 3 illustrates a use case example based on the method of FIG. 2A and FIG. 2B, in accordance with some embodiments of the present disclosure.

FIG. 3 is a flow diagram depicting steps of method 200 for the use case example 3 and is explained below:

User Requirement (User Objective): To maximize the ionic conductivity of the multi-component electrolyte with ethylene carbonate (EC) and dimethyl carbonate (DMC) as solvents and Lithium hexafluorophosphate ($LiPF_6$) as salt for lithium ion battery.

Modules Used: User Requirement Module, Component Selection Module, Operating Parameters Module, Initiation Module, Solver Module, Optimization Module.

Procedure

1. User Requirements Module: Enter the requirement as Composition Optimization. Select 'Salt Concentration' and 'Solvent Composition' from the list of properties to be optimized.
2. Component Selection Module: Select the components of the electrolyte from the database—
   a) $LiPF_6$ from the list of salts.
   b) EC and DMC from the list of solvents.
3. Operating Parameters Module: Temperature—333K and Pressure—1 atm.
4. Constraints Module
   1) Viscosity of the electrolyte within a range $\eta_{min} < \eta < \eta_{max}$.
   2) Salt concentration within a certain range (0.8 M to 1.2 M per se)
5. Initiation Module: The framework chooses to do MD simulations. The input files for MD having different composition of solvents from 0 to 100% mol/mass ratio is created for various salt concentrations from 0.8 to 1.2 M.
6. Solver Module: From MD simulations, the viscosity is calculated for a range of compositions. The output trajectory is post-processed to find the ionic conductivity.
7. Optimizer Module: To verify the maximum ionic conductivity achieved for a particular solvent composition at a particular salt concentration satisfies the viscosity constraint. If it is not satisfied, the Solver Module is run again for a different salt concentration. If it is satisfied, the user has the option to go for a different salt concentration or accept the result. User can also decide, based on the ionic conductivity drop, with respect to aging of the battery, whose analysis is by default done by the framework. Aging analysis is also one of the options that can be provided via the User Requirements Module.

Result: The final satisfactory output with the ratio of EC/DMC (Ratio) and the salt concentration that maximizes ionic conductivity with viscosity within the range is displayed on the screen or stored in the memory.

Example 3 above, is further discussed with respect to various bulk physical properties and dynamic properties that are considered by the method 200, unlike only bulk physical properties considered by existing methods.

The framework of the system 100, determines an ideal battery electrolyte by probing various the different aspects of its electrolytic behavior. These aspects include the bulk physical properties, which may or may not vary significantly during the operating period or variation with composition of electrolyte as well as the dynamic properties (e.g., lifetime of clusters) exhibited by the electrolyte that vary significantly at different operating conditions. While the existing works have focused on only the physical characteristics of the electrolytes the system 100 also takes into consideration the impact of dynamic properties on the overall electrolyte performance.

FIG. 4A through 4D are example results processed from simulation output data files depicting variation of multiple properties of a user defined electrolyte against variation of ratio of composition of solvents selected by the user as part of plurality of properties evaluated to find an optimum electrolyte composition, in accordance with some embodiments of the present disclosure.

Figure 4A:
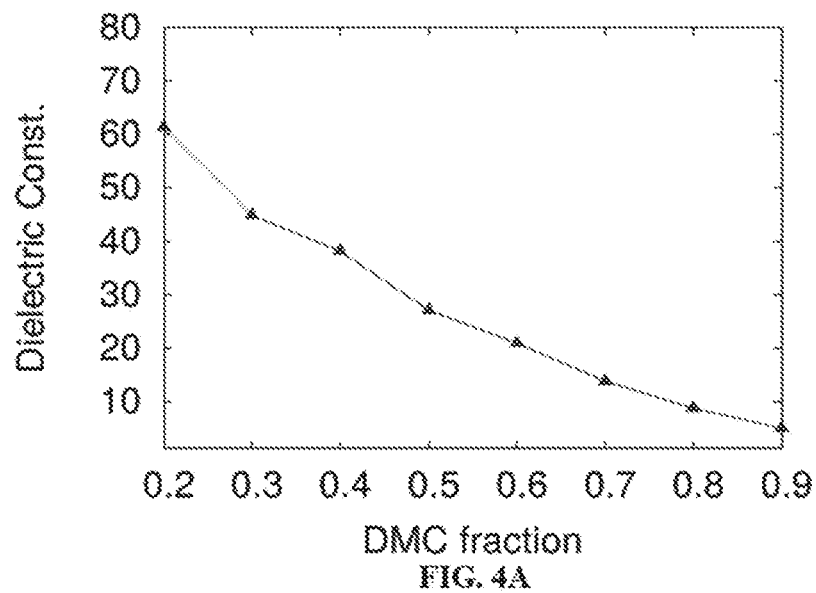
FIG. 4A through 4D are example results processed from simulation output data files depicting variation of multiple properties of a user defined electrolyte against variation of ratio of composition of solvents selected by the user as part of plurality of properties evaluated to find an optimum electrolyte composition, in accordance with some embodiments of the present disclosure.
Figure 4B:
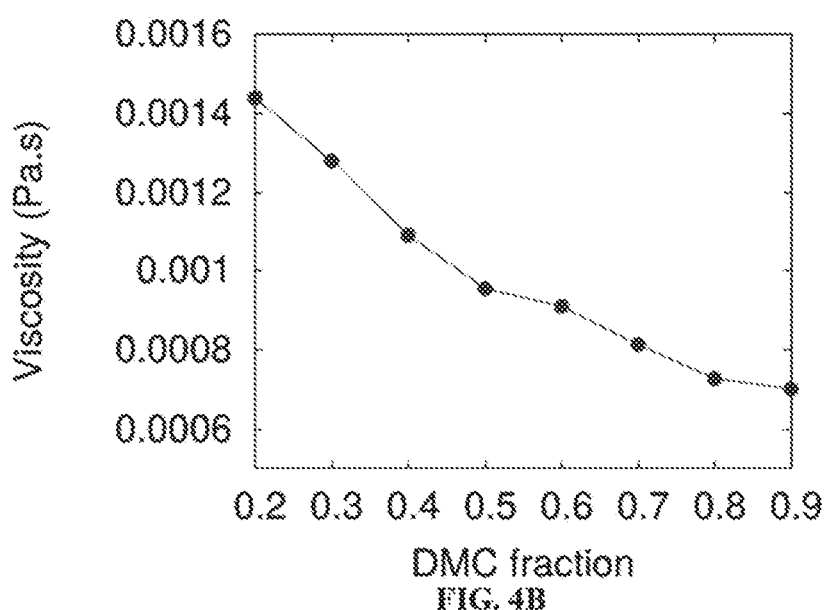
Figure 4C:
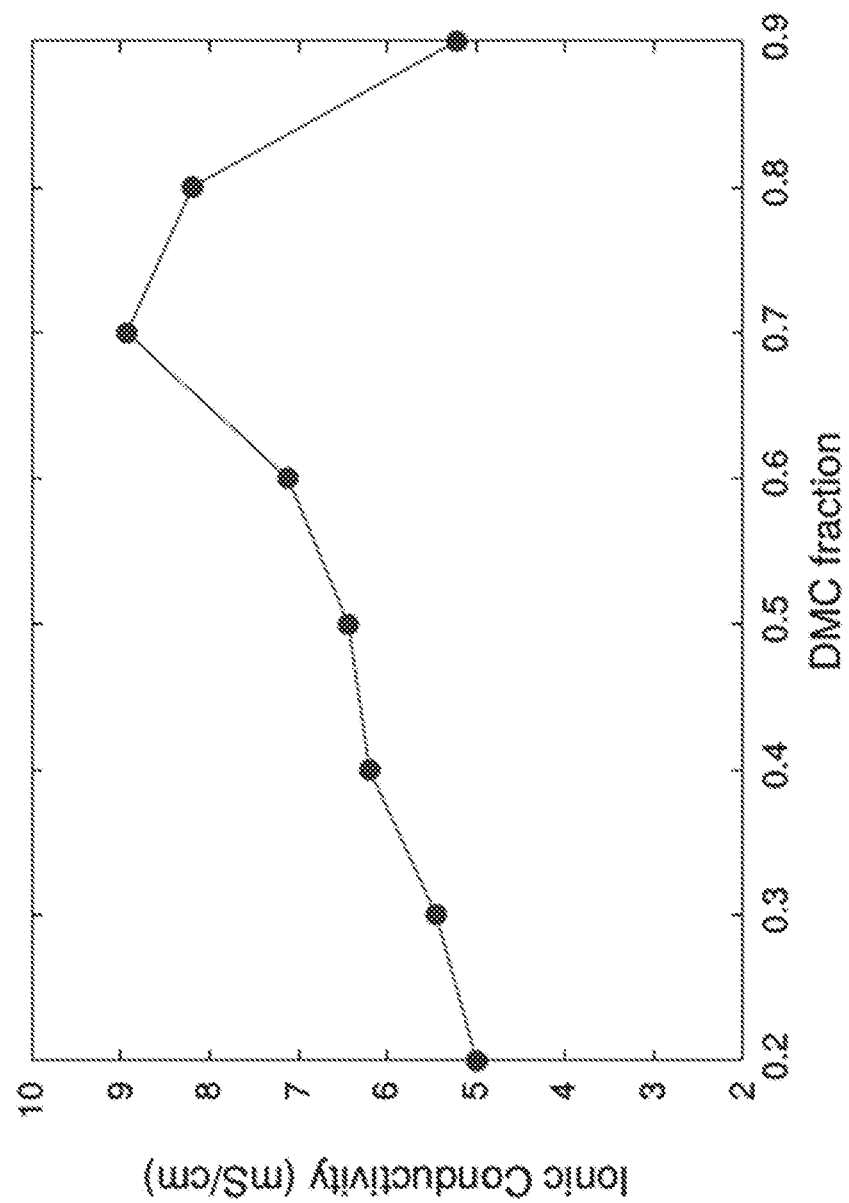

An example of the importance of dynamic properties in determining an ideal solvent mixture is described through the case study results depicted in FIG. 4A through 4D. In the example herein, user input requirement is to determine the ideal mixing ratio of DMC and EC as an electrolyte solvent mixture for lithium ion battery (LIB). FIGS. 4A and 4B reports the trend in the dielectric constant and viscosity for different solvent fractions computed by the plurality of simulation output data files in accordance with a set of predefined processes. It is observed that the physical properties show a continuously decreasing trend with increasing DMC fraction. From theory, it is known that an ideal electrolyte should have low viscosity to allow faster ion transport and high dielectric constant to ensure ion dissociation. However, if only these two factors are used, as in existing works, it would have been tricky to identify an ideal solvent ratio as considering one would lead to compromise in the other. The slightly higher value of ionic conductivity at a DMC fraction of 0.7 alone would have been a very feeble argument for selection of the electrolyte. Therefore, it is necessary to examine other mixture characteristics as well, in order to make a better decision as can be seen from FIG. 4C. Thus, the system 100 disclosed herein, via the selected simulation module, and the predefined processes additionally performs analysis with respect to additional properties.

Figure 4D:
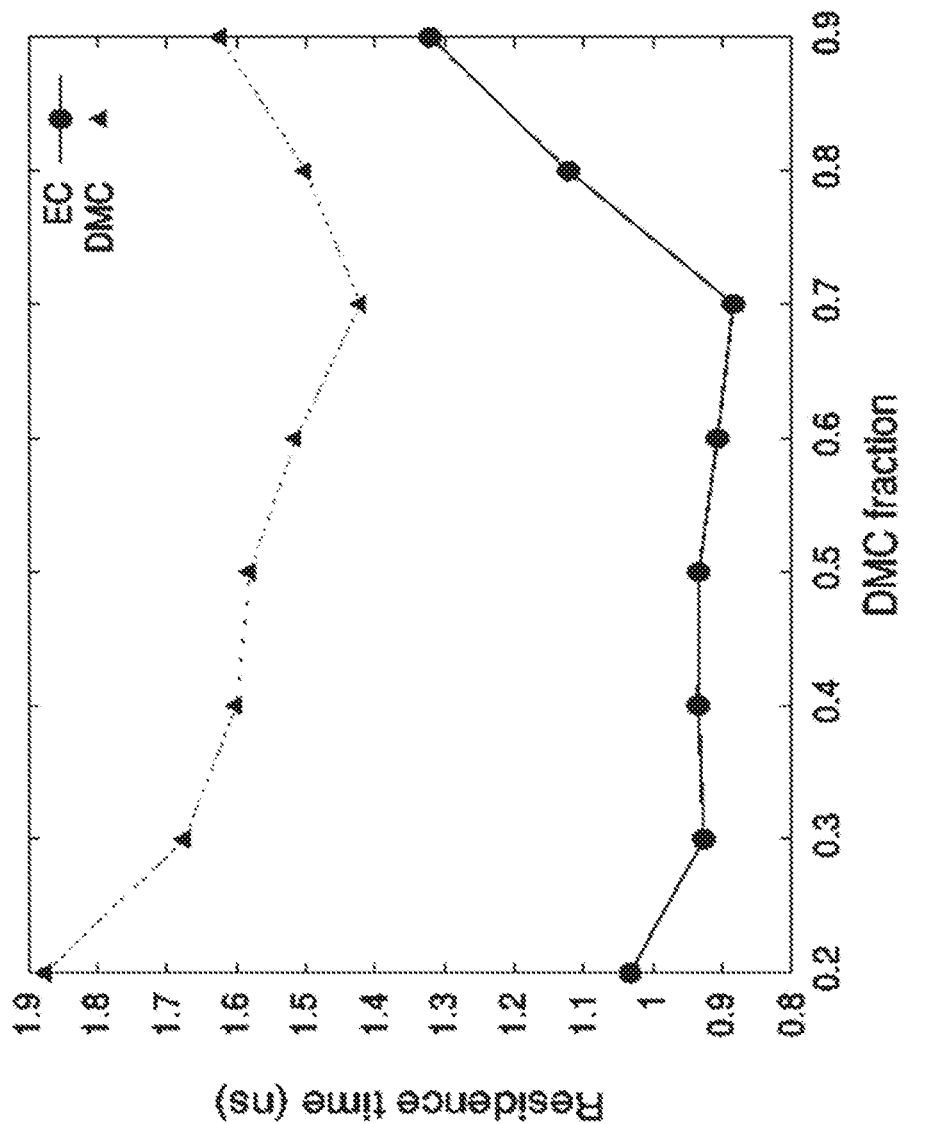

Each and every requirement in the first module has necessary set of workflows for invoking simulation techniques and their sequence. These workflows can be updated by an expert as and when the importance is observed. This importance comes from experience/knowledge updated over time. For example, analysis of the residence time values of solvent in the cation solvation shell for different fractions as shown in FIG. 4D solidifies the argument to choose 3:7 (or 0.7 fraction of DMC) ratio. Residence time analysis takes into consideration the solvation and de-solvation of ions by the solvent molecules that has direct impact on the charge transfer characteristics of the battery. Thus, the various kinds of molecular structures in the electrolyte also plays a key role in the decision-making process. This importance given to structural dynamics of molecules to identify the electrolyte makes our framework unique. Here, the lowest residence time of both the solvents at 3:7 EC:DMC fraction suggests that the solvation shell components are frequently changing, thus enhancing the electrolyte performance. It is to be understood that the analysis above is typically for the case under consideration and for some other cases, the lowest value of residence time would have been for some different composition.

Figure 4E:
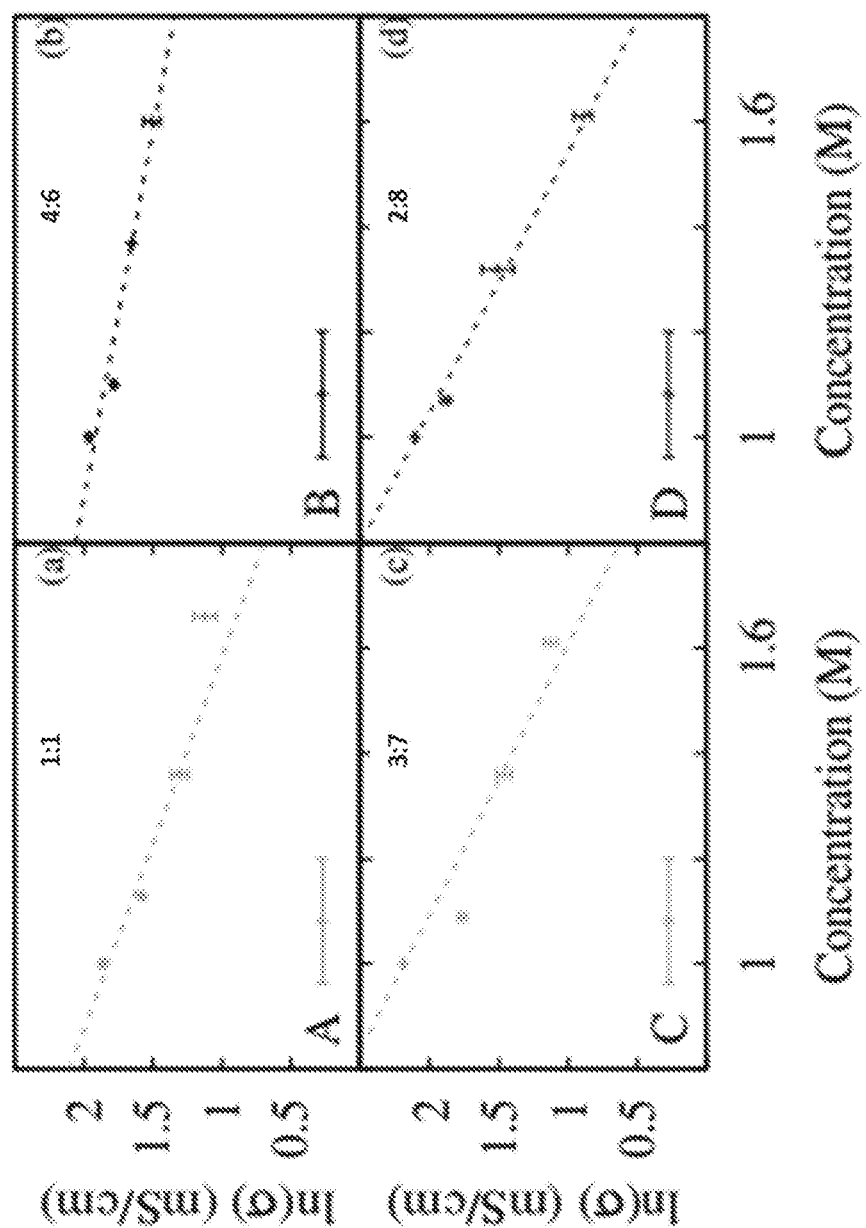
FIG. 4E is example result processed from simulation data files depicting aging of the battery for user selected solvents for varying ratio of solvent composition, in accordance with some embodiments of the present disclosure.

FIG. 4E is example result processed from simulation data files depicting aging of the battery for user selected solvents for varying ratio of solvent composition, in accordance with some embodiments of the present disclosure. Thus, in addition, as depicted in FIG. 4E, the method disclosed analyzes the ionic conductivity drop with increase in salt concentration (acting as an analogue for battery aging). and further an enhanced search is performed. Thus, framework of the system 100 enables to realize a more dependable choice compared to existing approaches by evaluating all the electrolyte properties including its structural and dynamic behavior. Thus, the method and system disclosed herein removes the arbitrariness while selecting any mixture composition.

Further, the system 100, in accordance with the user requirement, automatically identifies the set of modules to be run one after the other. For example, a combination one or more modules of the modules such as the component selection module, the constraints module, the operation parameter module, the initiation model, the optimization module and the like are triggered in specific identified sequence in accordance with the user objective identified in the user requirement. The sequence gets triggered once the user requirement is provided. The user is required to feed only the variables/numbers which are essential and will be prompted by the framework.

Figure 5A:
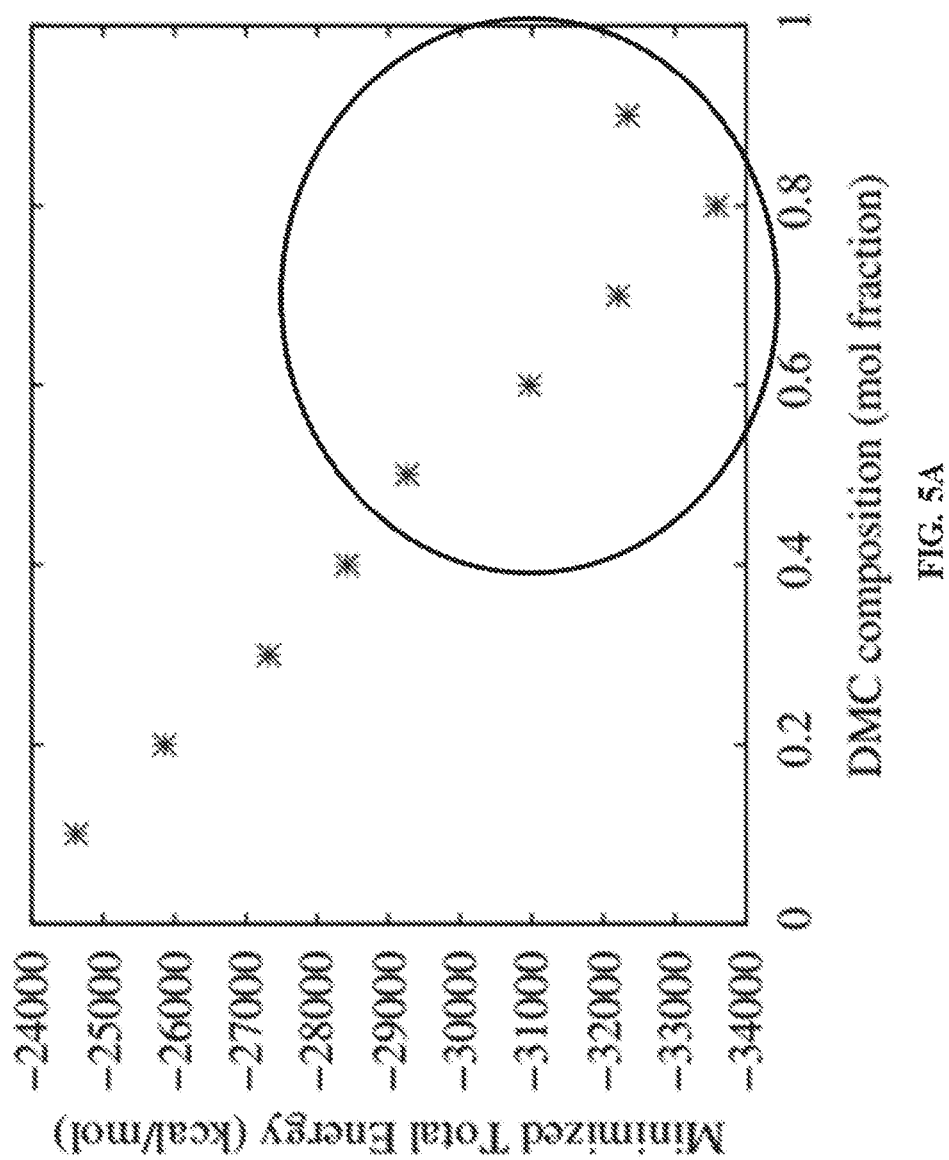
FIG. 5A and 5B depict a method for reduction in electrolyte evaluation time using the method of FIG. 2A and FIG. 2B, in accordance with some embodiments of the present disclosure.
Figure 5B:
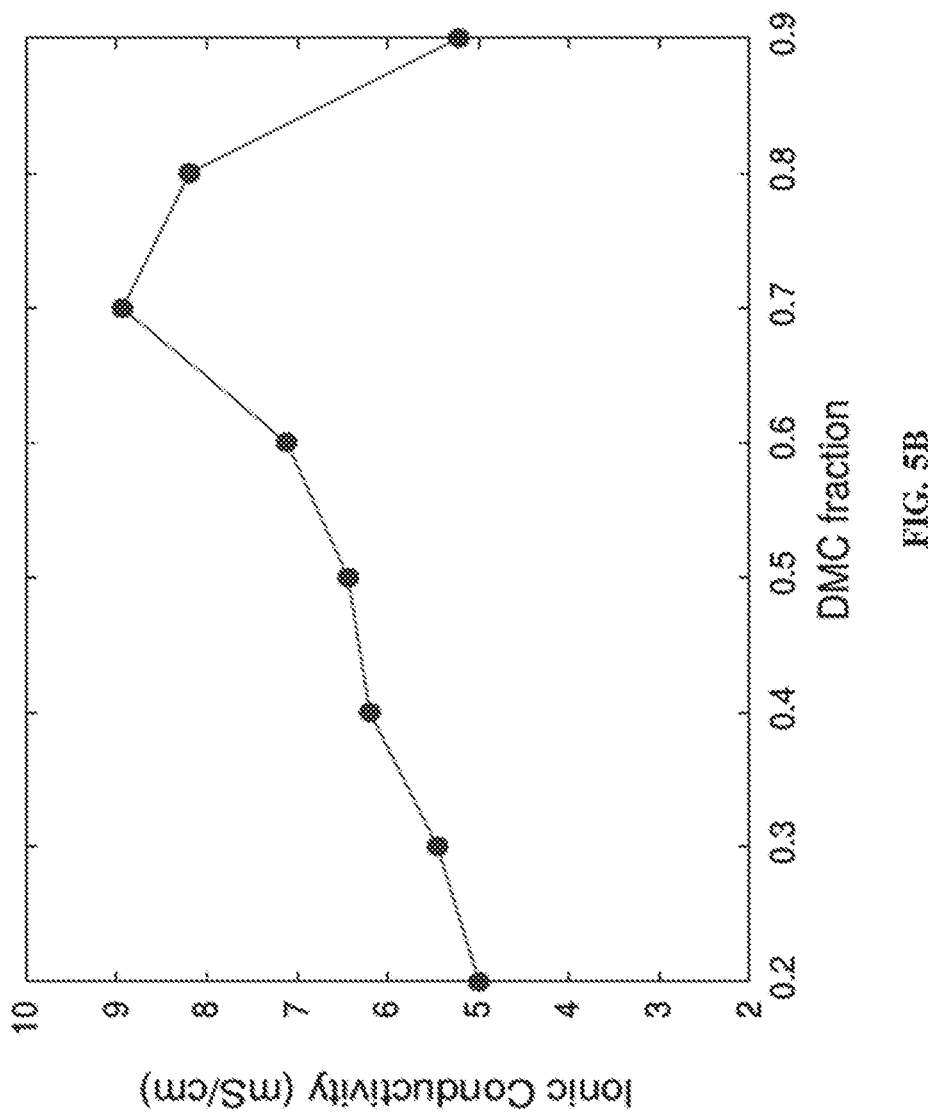

An arbitrary study of all the possible compositions of electrolytes can lead to huge computational cost. Therefore, a framework needs to be quick, and has to provide an intelligent way to reduce the sample space. While the possible composition ratios are comparatively lesser in case of binary mixtures, the number increases significantly for ternary mixtures or solvents with additives. Hence, if a promising region or zone can be obtained that forms a subset of all the possible combinations, the efforts for designing the electrolyte can be reduced. In the framework of the system 100, the framework can identify a potential region by analyzing the energetics. Initial screening can be done so as to extensively reduce the workload as well as provide prior idea of the approximate initial compositions. An example of this approach is depicted in FIG. 5A and 5B. Here, the minimized energies of the systems with various DMC fractions suggest the lowest energy zone between 0.6-1. After evaluating the ionic conductivities, the highest conductivity for the electrolyte with 3:7 EC:DMC composition is determined. This composition falls within the selected region of 0.6-1 DMC fraction. So, the entire analysis, including aging effect needs to be done only within this range. The final ideal electrolyte compositions are found within this range itself, validating the approach disclosed of reducing the sample space based on energetics. Even though this is the approach taken, FIG. 5B shows the entire range of DMC compositions to clearly show the validity of the assumption. Such an effective method for determining an ideal electrolyte composition has not been discussed by state-of-the-art methods.

Figure 6:
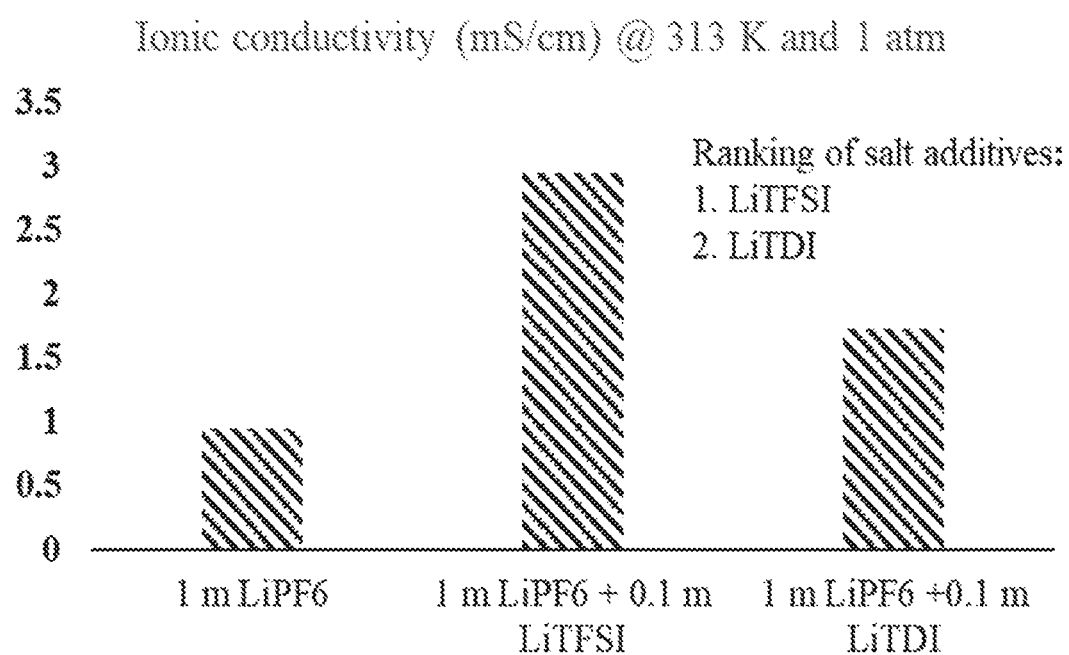
FIG. 6 depicts ranking of the salt additives using simulation provided by the method of FIG. 2A and FIG. 2B, in accordance with some embodiments of the present disclosure.

Furthermore, the user can probe the enhancement in electrolyte performance by an additive and rank them accordingly. FIG. 6 depicts ranking of the salt additives using simulation provided by the method of FIG. 2A and FIG. 2B, in accordance with some embodiments of the present disclosure As shown in FIG. 6, two salts (LITDI and LITFSI) are compared to check which one of the salt gives an ionic conductivity (power performance) enhancement to the 1 M LiPF$_6$ in EC based electrolyte. LiTFSI provides an improvement of 213% whereas LiTDI improves the ionic conductivity by 83%. Thus, both the additives are ranked accordingly.

Described below are some example predefined processes and their execution logic, which are used in conjunction with the selected simulation modules to analyze plurality of properties of the electrolyte and generate simulation output data.

It is to be understood that the following predefined processes are few examples and do not encompass all possible properties. The simulation technique discussed here as example is the Molecular Dynamics (MD) simulation.

Bulk Properties of Electrolytes

1. Dielectric constant: The dielectric constant is computed to determine its ability to dissociate the salt ions. From the atom positions obtained from the simulation trajectory of the electrolyte molecular system and their pre-determined partial charges, the dipole moment of the entire system is computed at regular time intervals, for e.g. every picosecond (ps). Further, the ensemble and time averaged dipole moment fluctuation ($\Delta\mu^2$) is computed using developed C++ codes. The system 100 considers the regime wherein fluctuations are stabilized to compute $\Delta\mu^2$, which is then substituted in the below equation to obtain the dielectric constant ($\varepsilon$).

$$\varepsilon = 1 + \langle\Delta\mu^2\rangle/(3V\varepsilon_o K_b T) \tag{1}$$

Here, V—Volume of the simulation box
T—Simulation Temperature
$K_b$—Boltzmann Constant
$\varepsilon_o$—vacuum permittivity 2. Molar conductivity: In order to compute molar conductivity, the positions data extracted and stored from the simulation trajectory as mentioned in, (1) Dielectric constant, are utilized. The ensemble and time averaged collective mean square displacement data for all possible ion pairs are obtained using developed codes that execute computations in parallel manner is obtained separately using developed C++ codes. These individual displacements are then further processed and time derivative of collective displacement in the long-time limit is obtained. It is further utilized to compute molar conductivity and ionic conductivity using a python code. For example, for the electrolyte of two ions, the following expression is used to obtain the molar conductivity:

$$\Lambda = (N_A e^2/6nK_b T)*\text{derivative} \qquad (2)$$

Here, $N_A$—Avogadro Number
T—Simulation Temperature
$K_b$—Boltzmann Constant
n—total number of ions (cations & anions)
e—electron charge Multiplication of this value with the salt concentration provides the ionic conductivity (a).

3. Viscosity: The data of atomic positions extracted at regular time interval of 1 ps is used as input for evaluating stress tensors. Once, the ensemble and time-averaged fluctuations of the off-diagonal stress tensor terms i.e. $Px_y$ (where $x \neq y$) is calculated, and then the shear viscosity ($\eta$) is computed using the Green-Kubo relation as given below $$\eta = (V/K_b T)*\int (dt <P_{xy}(t)P_{xy}(0)>) \qquad (3)$$

Here, V—Volume of the simulation box
T—Simulation Temperature
$K_b$—Boltzmann Constant 4. Self-diffusion coefficient: While using MD simulation as a simulation technique, for a specific type of ion/solvent, the positions of all such ions in the system are extracted from the non-periodic simulation trajectory and stored. Simulation frames are sampled at regular intervals of time (e.g. 1 ps) such that sampled frames are mostly uncorrelated. From the stored positions, the time-averaged mean square displacement (MSD) is computed, which is further subjected to ensemble averaging. These individual displacements are then further processed and time derivative of mean square displacement in the long-time limit is obtained. It is further utilized to compute. For example, in case of an electrolyte system, the self-diffusion coefficient of an ion is given by:

$$D = \text{limit}(MSD/6t) \qquad (4),$$

here, t–time

Structural and Dynamic Behavior Measurement
(Dynamic Properties)

5. Radial Distribution Function: Radial distribution function g(r) helps us to understand the structural arrangement of molecules influenced by their energetic interactions. For an atom x, the distribution of atoms y around it is computed by the following relation:

$$g_{x,y}(r) = 1/\rho[n(r)/4\pi r^2 dr] \qquad (5)$$

Here, $\rho$—Bulk number density
n(r)—No. of y atoms in differential volume $4\pi r^2 dr$ at distance r from atom x To calculate the g(r), the wrapped position coordinates of the atoms are first extracted using a python code. The different values of distance (r) are obtained by creating bins (generally 100) between the upper and the lower limit distance. For each bin i.e. the differential area, the distances of y atoms at a given distance r is computed and averaged for all such y atoms. This data for each r is divided by the bulk number density of atoms y, in order to normalize it.

6. Coordination Number: Coordination Number (CN) helps to measure the average number of y atoms around x (refer section 5) at a particular distance. It is obtained by integrating $g_{x,y}(r)$.

7. Residence Time: In order to understand the dynamics of the ion complexes formed, the mean residence time of the anion/solvent in the solvation shell around the cation is computed. For this, a Heaviside function H is defined such that H(t)=1 if the anion or solvent under consideration is present within a sphere of cut-off radius, $r_c$ centered at the cation i.e. $Li^+$. In case the distance is greater than the cut-off radius, the value of the function H(t) is 0. Thus, H(t) is a step function. The ensemble averaged auto correlation of the Heaviside function is evaluated using developed C++ codes. These values are used to obtain the value for correlation function C(t).

$$C(t) = <H(t)H(0)>/<H(0)H(0)> \qquad (6)$$

The decay of the curve of C(t) with time (t) is utilized to obtain the residence time $t_r$.

8. Potential of Mean Force (PMF): Analysis of the strength of interaction between molecules and ions are done by the measurement of PMF. This gives an indication about the mode of transport as well as potential precursors of solid electrolyte interphase while utilizing an electrolyte. We use two approaches to find PMF. For quick solution, g(r) is inverted as shown below:

$$PMF = -RT \ln(g(r)) \qquad (7)$$

Here, R is the Universal Gas constant. Otherwise, steered molecular dynamics (SMD) with umbrella sampling is utilized to measure PMF.

Cluster Analysis and Effect on Mode of Transport

9. Salt structure analysis: Ions of salt can exist in various forms in the electrolyte. It remains as completely separated ions, undissociated salt or as aggregates. Depending on the form the overall dynamics can change. Mode of charge transport can be diffusive or hopping based on the quantity and quality of these various structural entities.

The measurement of the different forms is done in the following manner: The trajectories of cations and anions are obtained. The C++ codes are used to measure the distance between the ions. The separation between various pairs of ions in the electrolyte is compared with a pre-defined or dynamically obtained cut-off distance to identify salt structure interactions ranging from solvent separated ion-pairs to aggregates that may lead to long chains.

10. Cluster charge measurement: The aggregates formed in the electrolytes can be smaller lumps or chain-like structures. The measurement of charges of these aggregates can give an idea of the mode of transport or polarization of the clusters. The developed codes can also evaluate charge distribution on the clusters of various kinds.

Thus, the provided is the method and system for in-silico optimization and design of electrolytes, enabling prediction of various properties of an electrolytic mixture of salts, solvents and various additives and its suitability for a given battery technology. The in-silico method shapes itself into an overall battery electrolyte property or component composition analyzer based on the user input.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software processing components located therein. Thus, the means can include both hardware means, and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A method for in-silico optimization and design of electrolytes, the method comprising:
    displaying, a User Interface (UI) implemented by one or more processors, to receive at least one user input, wherein the UI provides:
        a user requirement module for specifying a first user input comprising
            1) a battery from a list of battery types and
            2) a user requirement from a list of requirements indicating a user objective related to an electrolyte to be designed for use in the battery, wherein performance of the battery is to be optimized for the user requirement specified for the electrolyte;
        a component selection module for specifying a second user input comprising components of the electrolyte to be used for the battery, wherein the components comprise
            1) one or more salts,
            2) one or more solvents, and
            3) one or more additives;
        an operating parameters module to select a third user input comprising one or more operating parameters; and
        a constraints module for specifying a fourth user input comprising constraints on values of one or more properties of the electrolyte;
    selecting, via an initiation module implemented by the one or more processors, a simulation module from a plurality of simulation modules providing molecular modeling simulations, wherein selection of the simulation module is based on the user requirement specified in the user requirement module;
    performing, using the selected simulation module, implemented by the one or more processors, simulation to create simulation files, in accordance with the battery, the one or more salts, the one or more solvents and the additives;
    executing, using a solver module implemented by the one or more processors, the simulation files in accordance with the user requirement, the one or more operating parameters and the constraints on values of the one or more properties of the electrolyte, wherein the execution of simulation files provides a plurality of simulation output data files capturing variation of one or more properties of the electrolyte against the user requirement and
    verifying, using an optimization module implemented by the one or more processors, the one or more properties of the electrolyte against the constraints on values of one or more properties of electrolyte to check whether the one or more properties of the electrolyte are satisfied or not and if the one or more properties of the electrolyte are not satisfied, then triggering the constraints module and an initiation module to tweak on the values of the constraints of the one or more properties of the electrolyte to create simulation files; and re-executing the simulation files obtained for the tweaked values of the constraints of the electrolyte, by the optimization module implemented by the one or more processors, until the one or more properties of the electrolyte are satisfied, wherein the user requirement specifies requirement of an optimal battery performance against the specified at least one user input; and displaying on the UI, by the one or more processors, a set of simulation output data files from the plurality of simulation output data files that provide the optimal battery performance, and providing one or more optimal properties of the electrolyte or optimal components of electrolytes for operational requirement of the battery and/or recommending optimal operating conditions for obtaining the best performance out of the electrolyte.

2. The method of claim 1, wherein the one or more operating parameters comprise temperature and pressure at which the battery is expected to operate.

3. The method of claim 1, wherein one or more properties of the electrolyte comprise bulk physical properties and dynamic properties of the electrolyte.

4. The method of claim 1, wherein generating the plurality of simulation output data files is in accordance with a set of predefined processes followed during the execution of the simulation files.

5. The method of claim 1, wherein sequence for triggering one or more modules among the component selection module, the operating parameters module, the constraints module, the initiation module, the simulation module, the solver module and the optimization module is determined in accordance with the user objective related to the electrolyte in the user requirement module.

6. A system for in-silico optimization and design of electrolytes, the system comprising:

a memory storing instructions;

one or more Input/Output (I/O) interfaces; and one or more processors coupled to the memory via the one or more I/O interfaces, wherein the one or more processors configured by the instructions to:

display a User Interface (UI), implemented by the one or more processors, to receive at least one user input, wherein the UI provides:

a user requirement module for specifying a first user input comprising 1) a battery from a list of battery types and
2) a user requirement from a list of requirements indicating a user objective related to an electrolyte to be designed for use in the battery, wherein performance of the battery is to be optimized for the user requirement specified for the electrolyte;

a component selection module for specifying a second user input comprising components of the electrolyte to be used for the battery, wherein the components comprise 1) one or more salts,
2) one or more solvents, and
3) one or more additives;

an operating parameters module to select a third user input comprising one or more operating parameters; and a constraints module for specifying a fourth user input comprising constraints on values of one or more properties of the electrolyte;

select, via an initiation module implemented by the one or more processors, a simulation module from a plurality of simulation modules providing molecular modeling simulations, wherein selection of the simulation module is based on the user requirement specified in the user requirement module;

perform, using the selected simulation module implemented by the one or more processors, simulation to create simulation files, in accordance with the battery, the salts, the one or more solvents and the additives;

execute, using a solver module implemented by the one or more processors, the simulation files in accordance with the user requirement, the one or more operating parameters and the constraints on values of the one or more properties of the electrolyte, wherein the execution of simulation files provides a plurality of simulation output data files capturing variation of one or more properties of the electrolyte against the user requirement, and verify, using an optimization module implemented by the one or more processors, the one or more properties of the electrolyte against the constraints on values of one or more properties of electrolyte to check whether the one or more properties of the electrolyte are satisfied or not and if the one or more properties of the electrolyte are not satisfied, then triggering the constraints module and an initiation module to tweak on the values of the constraints of the one or more properties of the electrolyte to create simulation files; and re-execute the simulation files obtained for the tweaked values of the constraints of the electrolyte, by the optimization module implemented by the one or more processors, until the one or more properties of the electrolyte are satisfied, wherein the user requirement specifies requirement of an optimal battery performance against the specified at least one user input; and display on the UI, a set of simulation output data files from the plurality of simulation output data files that provide the optimal battery performance, and provide one or more optimal properties of the electrolyte or optimal components of electrolytes for operational requirement of the battery and/or recommending optimal operating conditions for obtaining the best performance out of the electrolyte.

7. The system of claim 6, wherein the one or more operating parameters comprise temperature and pressure at which the battery is expected to operate.

8. The system of claim 6, wherein one or more properties of the electrolyte comprise bulk physical properties and dynamic properties of the electrolyte.

9. The system of claim 6, wherein generating the plurality of simulation output data files is in accordance with a set of predefined processes followed during the execution of the simulation files.

10. The system of claim 6, wherein sequence for triggering one or more modules among the component selection module, the operating parameters module, the constraints module, the initiation module, the simulation module, the solver module and the optimization module is determined in accordance with the user objective related to the electrolyte in the user requirement module.

11. One or more non-transitory machine readable information storage mediums comprising one or more instructions, which when executed by one or more hardware processors causes a method for:

displaying a User Interface (UI) to receive at least one user input, wherein the UI provides: a user requirement module for specifying a first user input comprising
1) a battery from a list of battery types and
2) a user requirement from a list of requirements indicating a user objective related to an electrolyte to be designed for use in the battery, wherein performance of the battery is to be optimized for the user requirement specified for the electrolyte;

a component selection module for specifying a second user input comprising components of the electrolyte to be used for the battery, wherein the components comprise
1) one or more salts,
2) one or more solvents, and
3) one or more additives;

an operating parameters module to select a third user input comprising one or more operating parameters; and a constraints module for specifying a fourth user input comprising constraints on values of one or more properties of the electrolyte;

selecting via an initiation module a simulation module from a plurality of simulation modules providing molecular modeling simulations, wherein selection of the simulation module is based on the user requirement specified in the user requirement module;

performing using the selected simulation module simulation to create simulation files, in accordance with the battery, the one or more salts, the one or more solvents and the additives;

executing using a solver module the simulation files in accordance with the user requirement, the one or more operating parameters and the constraints on values of the one or more properties of the electrolyte, wherein the execution of simulation files provides a plurality of simulation output data files capturing variation of one or more properties of the electrolyte against the user requirement, and verifying, using an optimization module implemented by the one or more processors, the one or more properties of the electrolyte against the constraints on values of one or more properties of electrolyte to check whether the one or more properties of the electrolyte are satisfied or not and if the one or more properties of the electrolyte are not satisfied, then triggering the constraints module and an initiation module to tweak on the values of the constraints of the one or more properties of the electrolyte to create simulation files; and re-executing the simulation files obtained for the tweaked values of the constraints of the electrolyte, by the optimization module implemented by the one or more processors, until the one or more properties of the electrolyte are satisfied, wherein the user requirement specifies requirement of an optimal battery performance against the specified at least one user input; and displaying on the UI a set of simulation output data files from the plurality of simulation output data files that provide the optimal battery performance, and providing one or more optimal properties of the electrolyte or optimal components of electrolytes for operational requirement of the battery and/or recommending optimal operating conditions for obtaining the best performance out of the electrolyte.

12. The one or more non-transitory machine readable information storage mediums as claimed in claim 11, wherein the one or more operating parameters comprise temperature and pressure at which the battery is expected to operate.

13. The one or more non-transitory machine readable information storage mediums as claimed in claim 11, wherein one or more properties of the electrolyte comprise bulk physical properties and dynamic properties of the electrolyte.

14. The one or more non-transitory machine readable information storage mediums as claimed in claim 11, wherein generating the plurality of simulation output data files is in accordance with a set of predefined processes followed during the execution of the simulation files.

15. The one or more non-transitory machine readable information storage mediums as claimed in claim 11, wherein sequence for triggering one or more modules among the component selection module, the operating parameters module, the constraints module, the initiation module, the simulation module, the solver module and the optimization module is determined in accordance with the user objective related to the electrolyte in the user requirement module.

* * * * *